United States Patent [19]
Badger et al.

[11] Patent Number: 5,900,430
[45] Date of Patent: May 4, 1999

[54] CYTOKINE INHIBITORS

[75] Inventors: Alison Mary Badger, Bryn Mawr; Wanda Bernadette High, Wayne, both of Pa.

[73] Assignee: AnorMED, Inc., Langley, Canada

[21] Appl. No.: 08/779,418

[22] Filed: Jan. 7, 1997

Related U.S. Application Data

[63] Continuation of application No. 08/138,178, Oct. 15, 1993, Pat. No. 5,602,166, which is a continuation of application No. 07/887,628, May 22, 1992, abandoned, which is a continuation of application No. 07/657,578, Feb. 19, 1991, abandoned.

[51] Int. Cl.$^6$ .......................... A61K 31/40; A61K 31/55; A61K 31/44
[52] U.S. Cl. .......................... 514/409; 514/212; 514/278
[58] Field of Search .................... 514/409, 278, 514/212

[56] References Cited

U.S. PATENT DOCUMENTS 4,963,557  10/1990  Badger et al. ................... 514/278

*Primary Examiner*—Jerome D. Goldberg
*Attorney, Agent, or Firm*—Kate H. Murashige; Morrison & Foerster, LLP

[57] ABSTRACT

Invented are methods of inhibiting the production of cytokines, particularly inhibiting the production of interleukin-1 and inhibiting the production of tumor necrosis factor in a mammal in need thereof which comprises administering to such mammal an effective amount of an azaspirane derivative.

16 Claims, No Drawings

CYTOKINE INHIBITORS

This is a continuation of application Ser. No. 08/138,178, filed Oct. 15, 1993, now U.S. Pat. No. 5,602,266, which is a continuation of application Ser. No. 07/887,628, filed May 22, 1992, now abandoned, which is a continuation of application Ser. No. 07/657,578, filed Feb. 19, 1991, now abandoned.

BACKGROUND OF THE INVENTION

This invention relates to a method of inhibiting the production of cytokines, particularly inhibiting the production of interleukin-1 and inhibiting the production of tumor necrosis factor, in a mammal, including a human, in need thereof which comprises administering to such mammal an effective, cytokine production inhibiting amount of a substituted azaspirane.

Badger et al., U.S. Pat. No. 4,963,557 issued October 16, 1990, discloses compounds of the formula

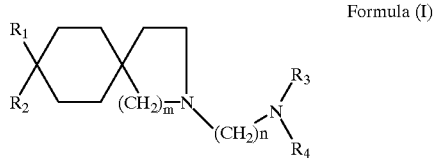

Formula (I)

wherein: n is 3–7; m is 1 or 2; $R_1$ and $R_2$ are the same or different and are selected from hydrogen or straight chain, branched chain or cyclic alkyl, provided that the total number of carbon atoms contained by $R_1$ and $R_2$ when taken together is 5–10; or $R_1$ and $R_2$ are joined together to form a cyclic alkyl group having 3–7 carbon atoms; $R_3$ and $R_4$ are the same or different and are selected from hydrogen or straight chain alkyl having 1–3 carbon atoms; or $R_3$ and $R_4$ are joined together with the nitrogen atom to form a heterocyclic group having 5–8 atoms; or a pharmaceutically acceptable salt or hydrate or solvate thereof. Badger et al., also discloses that such compounds have utility in inducing immune suppression via induction of suppressor cell like activity based on their activity in the adjuvant-induced arthritis test in rats and their activity in the suppressor cell assay. The adjuvant arthritis test is useful for detecting compounds which are inhibitors of prostanoid synthesis, but is of no utility for disclosing or suggesting compounds which are inhibitors of cytokine production, particularly compounds which are inhibitors of interleukin-1 (IL-1) and/or tumor necrosis factor (TNF). The suppressor cell assay is useful for detecting immunosuppressive compounds but is of no known utility for disclosing or suggesting compounds which are inhibitors of cytokine production, particularly compounds which are inhibitors of IL-1 and/or TNF production.

Cytokines are biological substances produced by a variety of cells, such as monocytes or macrophages. Cytokines affect a wide variety of cells and tissues and are important and critical inflammatory mediators of a wide variety of disease states and conditions. The inhibition of these cytokines is of benefit in controlling, reducing and alleviating many of these disease states.

SUMMARY OF THE INVENTION

This invention relates to a method of inhibiting the production of cytokines, particularly inhibiting the production of interleukin-1 (IL-1) and inhibiting the production of tumor necrosis factor (TNF), in a mammal including a human, in need thereof which comprises administering to such mammal an effective, cytokine production inhibiting amount of a compound of the Formula

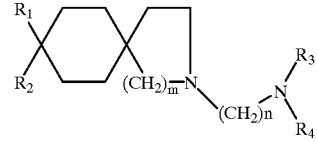

Formula 1 wherein:
n is 3–7;
m is 1 or 2;
$R_1$ and $R_2$ are the same or different and are selected from hydrogen or straight chain, branched chain or cyclic alkyl, provided that the total number of carbon atoms contained by $R_1$ and $R_2$ when taken together is 5–10; or $R_1$ and $R_2$ are joined together to form a cyclic alkyl group having 3–7 carbon atoms;
$R_3$ and $R_4$ are the same or different and are selected from hydrogen or straight chain alkyl having 1–3 carbon atoms; or $R_3$ and $R_4$ are joined together with the nitrogen atom to form a heterocyclic group having 5–8 atoms;
or a pharmaceutically acceptable salt or hydrate or solvate thereof.

The discovery of a compound which inhibits cytokine production provides a therapeutic approach for diseases in which excessive or unregulated cytokine production is implicated.

DETAILED DESCRIPTION OF THE INVENTION

The preparation of all compounds of Formula (I) and pharmaceutically acceptable salts, hydrates and solvates thereof is disclosed in U.S. Pat. No. 4,963,557 issued to Badger et al. on Oct. 16, 1990 the entire disclosure of which is hereby incorporated by reference.

By the term "cytokine" as used herein is meant any secreted polypeptide that affects the functions of other cells, and is a molecule which modulates interactions between cells in the immune or inflammatory response. A cytokine includes, but is not limited to monokines and lymphokines regardless of which cells produce them. For instance, a monokine is generally referred to as being produced and secreted by a mononuclear cell, such as a macrophage and/or monocyte but many other cells produce monokines, such as natural killer cells, fibroblasts, ip basophils, neutrophils, endothelial cells, brain astrocytes, bone marrow stromal cells, epideral keratinocytes, and B- lymphocytes. Lymphokines are generally referred to as being produced by lymphocyte cells. Examples of cytokines include, but are not limited to, interleukin-1 (IL-1), tumor necrosis factor-alpha (TNFα) and tumor necrosis factor beta (TNFβ).

By the term "cytokine production inhibiting amount" is meant an effective amount of a compound of Formula (I) which will, when given for the treatment, prophylacticaly or therapeutically, of any disease state which is exacerbated or caused by excessive unregulated cytokine production, cause a decrease in the in vivo levels of the cytokine to normal or below normal levels.

By the term "inhibiting the production of cytokines" is meant
a) a decrease of excessive in vivo cytokine levels in a mammal, including a human, to normal levels or below normal levels by inhibition of the in vivo release of cytokines by all cells, including but not limited to monocytes or macrophages;

b) a down regulation, at the level of transcription or translation, of excessive in vivo cytokine levels in a mammal, including a human, to normal levels or below normal levels; or c) a down regulation, by inhibition of the direct synthesis of a cytokines as a postranslational event.

By the term "inhibiting the production of IL-1" is meant a) a decrease of excessive in vivo IL-1 levels in a mammal, including a human, to normal levels or below normal levels by inhibition of the in vivo release of IL-1 by all cells, including but not limited to monocytes or macrophages;

b) a down regulation, at the level of transcription or translation, of excessive in vivo IL-1 levels in a mammal, including a human, to normal levels or below normal levels; or c) a down regulation, by inhibition of the direct synthesis of IL-1 as a postranslational event.

By the term "inhibiting the production of TNF" is meant a) a decrease of excessive in vivo TNF levels in a mammal, including a human, to normal levels or below normal levels by inhibition of the in vivo release of TNF by all cells, including but not limited to monocytes or macrophages;

b) a down regulation, at the level of transcription or translation, of excessive in vivo TNF levels in a mammal, including a human, to normal levels or below normal levels; or c) a down regulation, by inhibition of the direct synthesis of TNF as a postranslational event.

As TNF-β (also known as lymphotoxin) has close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

Studies have indicated that TNF is a serum glycoprotein and that its activity is associated with a high molecular weight components. Mouse and rabbit TNF have been isolated, as has human TNF which sequence is taught in U.S. Pat. No. 4,879,226, issued Nov. 7, 1989. TNF is synthesized as a prohormone and subsequently cleaved at several sites to yield the mature hormone. While the active polypeptide itself has been evaluated for treatment of tumors due to its earlier reported antineoplastic activity, this administration has not been without many severe toxicities. Overproduction of TNF has further been implicated in the pathogenesis of endotoxin/septic shock. See, e.g., Carswell et al., *Proc. Natl. Acad. Sci. USA*, 72, 3666–3670 (1975). Endotoxin comprises the lipolysaccharide component of the cell wall of gram-negative bacteria, and is a macrophage activator which induces the synthesis and secretion of cytokines and other biologically active molecules such as TNF. In sepsis, TNF production leads to hypotension, vascular endothelial permeability, and organ damage, i.e., some of the results of endotoxic shock. Adult Respiratory Distress Syndrome (ARDS) is frequently associated with sepsis and multiple organ failure which has led to the suggestion of a role for TNF in the pathogenesis of ARDS. TNF is also the agent responsible for the weight loss (cachexia) found in chronic catabolic disease states, such as long term parasitic and viral infections, and in malignancies. This weight loss is a handicap to recovery and may even be fatal.

TNF also appears to play a role as an early product in the inflammatory response. See, e.g., Old, *Nature*, 330, 602–03 (1987). It further appears that among the cytokines, while TNF production precedes and augments the function of IL-1 and other cytokines there is no clear data on how the relationship among these molecules contributes to inflammation-related disease states. TNF activates macrophages and enhances their cytotoxic potential in vitro. TNF has been shown to be chemotactic for monocytes, suggesting that the production of TNF at sites of injury may function to recruit additional macrophages and activate those macrophages already present.

Among the various mammalian conditions for which TNF is implicated in mediating or exacerbating are rheumatiod arthritis, rheumatiod spondylitis, osteoarthritis, gouty arthritis and other arthritic conditions; sepsis, septic shock, endotoxic shock, gram negative sepsis, toxic shock syndrome, adult respiratory distress syndrome, malaria, pulmonary inflammatory disease, bone resorption diseases, reperfusion injury, graft vs. host reaction, fever and myalgias due to infection, such as influenza, cachexia secondary to infection or malignancy, cachexia secondary to acquired immune deficiency syndrome (AIDS), AIDS, keloid formation, scar tissue formation, Crohn's disease, ulcerative colitis, or pyresis.

The human acquired immune deficiency syndrome (AIDS) results from the infection of lymphocytes, and perhaps macrophages, with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. There is a continuing need for agents which are useful in inhibiting further disease progress in an already infected individual. TNF has been implicated in various roles with the AIDS virus as described below.

Clouse et al., *J. Immunol.*, 142, 431 (1989), discuss that monokines secreted by activated human monocytes induced elevated levels of HIV expression in a chronically infected human T cell clone. The monokine involved in this process was identified as TNFα.

Gowda et al., *J. Immunol.*, 142, 773 (1989), discuss that T cell activation is required for HIV entry and HIV-dependent cell fusion.

Zagury et al., *Science*, 231, 850 (1986), discuss that T cell activation is required for HIV gene expression.

Wright et al., *J. Immunol.*, 141, 99 (1988), discuss that monocytes from HIV-infected patients produced large amounts of TNFα and interleukin-1 (IL-1 hereinafter) upon culturing in vitro.

Beutler et al., *Nature (London)*, 316, 552–554 (1985), discuss the role of TNFα in cachexia.

Chiebowski et al., *Nutr. Cancer*, 7, 85 (1985), discuss HIV-associated states of cachexia and muscle degradation.

Lahdevirta et al., *The American J. Med.*, 85, 289 (1988), discuss that TNFα is involved in the HIV-associated states of cachexia and muscle degradation.

Wright et al., *J. Immunol.* 141(1):99–104 (1988) suggests a possible role for TNF in AIDS cachexia by elevated serum TNF and high levels of spontaneous TNF production in peripheral blood monocytes from patients. Folks et al., *Proc. Natl. Acad. Sci, USA*, 86:2365–2368 (1989) suggests that TNF is implicated in the stimulation of iral replication of latent HIV in T-cell and macrophage lines hich can be induced by TNF.

Osborn et al., *Proc. Natl. Acad. Sci, USA*, 86:2336–2340 (1989) suggests that a molecular mechanism for the virus inducing activity of TNF is due to TNF's ability to activate a gene regulatory protein (NF-kB) found in the cytoplasm of cells, which promotes HIV replication through binding to a viral regulatory gene sequence (LTR).

Yale University, European Patent Application Publication Number 0,230,574 A2, published Aug. 6, 1987, claims a method for producing pharmaceutical compositions for treating patients infected with LAV/HTLV III virus wherein such composition contains a compound which inhibits the production and/or the activity of mononuclear cell derived cytotoxic factors, such as lymphotoxin, tumor necrosis factor, leukoregulin and natural killer cytotoxic factor.

It is concluded from the above references that compounds which inhibit the production of TNF will have a therapeutic effect on the treatment of acquired immune deficiency syndrome (AIDS) and/or the treatment of AIDS related complications.

Interleukin-l (IL-1) has been demonstrated to mediate a variety of biological activities thought to be important in immunoregulation and other physiological conditions such as inflammation [See, e.g. Dinarello et al., *Rev. Infect Disease*, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels. Specifically, there are several disease states in which excessive or unregulated IL-1 production by monocytes and/or macrophages is implicated in exacerbating and/or causing the disease. These include rheumatoid arthritis [See, e.g., Fontana et al., *Arthritis Rheum*, 22, 49–53 (1982)]; osteoarthritis [See, e.g., Wood et al., *Arthritis Rheum*. 26, 975 (19–83)]; toxic shock syndrome [See, e.g., Ikejima and Dinarello, *J. Leukocyte Bioloqy*, 37, 714 (1985)]; other acute or chronic inflammatory disease states such as the inflammatory reaction induced by endotoxin [See, e.g., Habicht and Beck, *J. Leukocyte Biology*, 37, 709 (1985)]; and other chronic inflammatory disease states such as tuberculosis. [See, e.g., Chesque et al., *J. Leukocyte Biology*, 37, 690 (1985)]. Benjamin et al., "Annual Reports in Medicinal Chemistry, 20", Chapter 18, pages 173–183 (1985), Academic Press, Inc., disclose that excessive IL-1 production is implicated in: psoriatic arthritis, Reiter's syndrome, rheumatoid arthritis, osteoarthritis, gout, traumatic arthritis, rubella arthritis, and acure synovitis.

Dinarello, *J. Clinical Immunology*, 5, (5), 287–297 (1985), reviews the biological activities which have been attributed to IL-1 and such activities are summarized in Table A.

TABLE A

Biological Activities Attributed to IL-1
Fever (in rabbits, mice and rats)
Hypoferremia
Hypozincemia
Hypercupremia
Increased
  Blood neutrophils
  Hepatic acute-phase proteins
  Bone resorption, including; osteoprosis and Paget's disease
  Cartilage breakdown
  Muscle proteolysis
  Slow-wave sleep
  Endothelial procoagulant
  Chondrocyte proteases
  Synovial collagenase
  Endothelial neutrophil adherence
  Neutrophil degranulation
  Neutrophil superoxide
  Interferon production
Proliferation of
  Fibroblasts
  Glial cells
  Mesangial cells
  Synovial fibroblasts
  EBV B-cell lines
  Chemotaxis of
  Monocytes
  Neutrophils
  Lymphocytes
Stimulation of $PGE_2$ in
  Hypothalamus
  Cortex
  Skeletal muscle
  Dermal fibroblast
  Chondrocyte
  Macrophage/monocyte
  Endothelium ($PGI_2$)
Decreased
  Hepatic albumin synthesis
  Appetite
  Brain binding of opioids
Augmentation of
  T-cell responses
  B-cell responses
  NK activity
  IL-2 production
  Lymphokine production.

The discovery of a compound which inhibits Il-1 production provides a therapeutic approach for diseases in which excessive or unregulated Il-1 production is implicated.

It has now been discovered that compounds of Formula (I) and pharmaceutically acceptable salts or hydrates or solvates thereof are useful for inhibiting cytokine production in a mammals, including humans, in need of such inhibition.

An effective, cytokine production inhibiting amount of a compound of Formula (I) or a pharmaceutically acceptable salt or hydrate or solvate thereof is useful in treating, prophlactically or thereapeutically, any disease state in a mammal, including a human, which is exacerbated or caused by excessive or unregulated cytokine production. Preferably, the inhibited cytokines are IL-1 and TNF. Preferably, the disease state is selected from; increased bone resorption, endotoxic shock, cachexia secondary to acquired immune deficiency syndrome (AIDS), AIDS or malaria. Particularly preferred is the disease state of increased bone resorption, including osteoporosis and Paget's disease.

This invention relates to a method of inhibiting the production of cytokines, particularly inhibiting the production of IL-1 and TNF, in a mammal, including a human, in need thereof which comprises administering an effective, cytokine production inhibiting amount of a compound of Formula (I) or a pharmaceutically acceptable salt or hydrate or solvate thereof. A compound of Formula (I) or a pharmaceutically acceptable salt or hydrate or solvate thereof can be administered to such mammal, including a human, in a conventional dosage form prepared by combining a compound of Formula (I), or a pharmaceutically acceptable salt or hydrate or solvate thereof, with a conventional pharmaceutically acceptable carrier or diluent according to known techniques, such as those described in Badger et al. U.S. Pat. No. 4,963,557 issued on Oct. 16, 1990.

It will be recognized by one of skill in the art that the form and character of the pharmaceutically acceptable carrier or diluent is dictated by the amount of active ingredient with which it is to be combined, the route of administration and other well-known variables. A compound of Formula (I) or a pharmaceutically acceptable salt or hydrate or solvate thereof is administered to a mammal, including a human, in need of inhibition of cytokine production in an amount sufficient to inhibit such excessive cytokine production to the extent that it is regulated down to normal levels. The route of administration may be oral, parenteral or topical. The term parenteral as used herein includes intravenous, intramuscular, subcutaneous, intranasal, intrarectal, intravaginal or intraperitoneal administration. The subcutaneous and intramuscular forms of parenteral administration are generally preferred. The daily oral dosage regimen will preferably be from about 0.1 to about 1000 mg/kilogram of total body weight. The daily parenteral dosage regimen will preferably be from about 0.1 to about 800 mg per kilogram (kg) of total body weight, most preferably from about 1 to about 100 mg/kg. The daily topical dosage regimen will preferably be from about 1 mg to about 100 mg per site of administration. It will be recognized by one of skill in the art that the optimal quantity and spacing of individual dosages of a compound of Formula (I) or a pharmaceutically acceptable salt or hydrate or solvate thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt or hydrate or solvate thereof given per day for a defined number of days, can be ascertained by those skilled in the art using conventional course of treatment determination tests.

Without further elaboration, it is believed that one skilled in the art can, using the preceding description, utilize the present invention to its fullest extent.

As used herein, the term "compound 1" refers to a compound of Formula (I) where $R_1$ and $R_2$ are propyl, $R_3$ and $R_4$ are methyl, m is 1 and n is 3 which is N,N-dimethyl-8,8-dipropyl-2-azaspiro[4,5]decane-2-propanamine.

MEASUREMENT OF IN VIVO CYTOKINE ACTIVITY

Levels of TNF were measured using a modification of the basic sandwich ELISA method described in Winston et al., *Current Protocols in Molecular Biology*, Pg. 11.2.1, Ausubel et al., Ed. (1987) John Wiley and Sons, New York, USA. The ELISA employed a hamster monoclonal anti-mouse TNF (Genzyme, Boston, Mass., USA) as the capture antibody and a polyclonal rabbit anti-murine TNF (Genzyme, Boston, Mass., USA) as the detecting antibody. TNF levels in mouse samples were calculated from a standard curve generated with recombinant murine TNF (Genzyme, Boston, Mass., USA). TNF levels determined by ELISA correlated with levels detected by the L929 bioassay of Ruff et. al., *J. Immunol.* 125:1671–1677 (1980), with 1 Unit of activity in the bioassay corresponding to 70 picograms (pg) of TNF in the ELISA. The ELISA detected levels of TNF down to 25 pg/ml.

Lipopolysalcharide stimulated macrophages from adjuvant arthritic rats treated with compound 1 produce 50% less TNF than untreated controls.

Levels of IL-1 were measured using the method described in Simon, P. L. et al., *J. Immunol. Methods* 84:85–94, 1985. This method is based on the production of interleukin-2 from the EL-4 murine t-cell lymphoma cell line in the presence of $2-5 \times 10^{-7}$ M of calcium ionophore A23187.

Compound 1 demonstrated a positive in vivo response of about 75% reduction in levels of Il-1 in the above assay.

what is claimed is:

1. A method of treating a disease state which is exacerbated or caused by excessive or unregulated cytokinine production in a mammal, including a human, which comprises administering to such mammal an effective, cytokine production inhibiting amount of a compound of the Formula

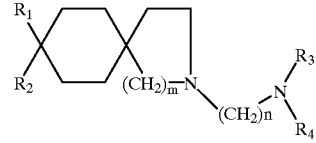

Formula (I)

wherein:

n is 3–7;

m is 1 or 2;

$R_1$ and $R_2$ are the same or different and are selected from hydrogen or straight chain, branched chain or cyclic alkyl, provided that the total number of carbon atoms contained by RI and $R_2$ when taken together is 5–10; or $R_1$ and $R_2$ are joined together to form a cyclic alkyl group having 3–7 carbon atoms;

$R_3$ and $R_4$ are the same or different and are selected from hydrogen or straight chain alkyl having 1–3 carbon atoms; or $R_3$ and $R_4$ are joined together with the nitrogen to form a heterocyclic group having 5–8 atoms; or a pharmaceutically acceptable salt or hydrate or solvate thereof wherein the disease state which is treated is selected form the group consisting of rheumatoid arthritis, rheumatoid spondylitis, gouty arthritis, sepsis, septic shock, gram negative sepsis, toxic shock syndrome, adult repsiratory distress syndrome, pulmonary infammatory disease, reperfusion injury, graft vs. host reaction, influenza, cachexia secondary to infection or malignancy, cachexia secondary to acquired immune deficiency syndrome (AIDS), AIDS, keloid formation, scar tissue formation, Crohn's disease, ulcerative colitis and pyresis.

2. The method of claim 1 wherein the compound is N,N-dimethyl-8,8-dipropyl-2-azaspiro[4,5]decane-2-propanamine dihydrochloride.

3. The method of claim 2 wherein the mammal is afflicted with Cachexia secondary to acquired immune deficiency syndrome (AIDS).

4. The method of claim 2 wherein the mammal is afflicted with acquired immune deficiency syndrome (AIDS).

5. The method of claim 2 wherein the cytokine which is inhibited is interleukin-1.

6. The method of claim 5 wherein the desired therapeutic effect is the inhibition of prostaglandin production.

7. The method of claim 2 wherein the cytokine which is inhibited is tumor necrosis factor.

8. The method of claim 2 wherein the compound is administered orally.

9. The method of claim 8 wherein from about 1 to about 2000 mg of compound are administered per day.

10. The method of claim 2 wherein the compound is administered parenterally.

11. The method of claim 10 wherein from about 0.1 to about 1000 mg of compound are administered per day.

12. The method of claim 2 wherein the compound is administered by inhalation.

13. The method of claim 12 wherein from about 10 to about 100 mg of compound are administered per day.

14. The method of claim 2 wherein the compound is administered topically.

15. The method of claim 14 wherein from about 1.5 mg/kg to about 500 mg/kg of body weight are administered per day.

16. The method of claim 1 wherein the compound is N,N-dimethyl-8,8-dipropyl-2-azaspiro[4,5]decane-2-propanamine; or a pharmaceutically acceptable salt or hydrate or solvate thereof.

* * * * *